United States Patent [19]

Anderson, Jr.

[11] Patent Number: 4,690,437
[45] Date of Patent: Sep. 1, 1987

[54] LOW PRESSURE FITTING

[75] Inventor: James M. Anderson, Jr., Arlington Heights, Ill.

[73] Assignee: Alltech Associates, Inc., Deerfield, Ill.

[21] Appl. No.: 834,003

[22] Filed: Feb. 27, 1986

[51] Int. Cl.$^4$ .............................................. F16L 17/02
[52] U.S. Cl. ..................... 285/356; 55/386; 285/911; 285/339; 285/343
[58] Field of Search ............... 285/356, 911, 353, 339, 285/343; 55/3896; 210/656, 198.2

[56] References Cited

U.S. PATENT DOCUMENTS

| | | | |
|---|---|---|---|
| 1,883,273 | 10/1932 | Zerk | 285/356 |
| 1,937,865 | 12/1933 | Baker | 285/911 |
| 2,715,536 | 8/1955 | Shuptrine | 285/356 |
| 3,434,744 | 3/1969 | Yoke | 285/356 |
| 3,791,522 | 2/1974 | Eisenbeiss | 55/386 |
| 3,954,291 | 5/1976 | Gonner | 285/356 |
| 4,026,803 | 5/1977 | Abrahams | 55/386 |
| 4,083,702 | 4/1978 | Hartigan | 55/386 |
| 4,394,263 | 7/1983 | Dosch | 55/386 |
| 4,529,230 | 7/1985 | Fatula | 285/911 |
| 4,565,632 | 1/1986 | Hatch | 55/386 |

FOREIGN PATENT DOCUMENTS 669111 3/1952 United Kingdom ................ 285/356

OTHER PUBLICATIONS

Valco Instruments Publication, pp. 1–8, received by PTO 6/29/83.

Applied Spectroscopy Publication, 2 pages, vol. 30, No. 2, p. 237, Mar./Apr. 1976.

Primary Examiner—Cornelius J. Husar
Assistant Examiner—Eric K. Nicholson
Attorney, Agent, or Firm—Lee, Smith & Zickert

[57] ABSTRACT

The disclosed fitting connects a tubing end to a fluid conducting member which have a fluid port and end walls surrounding the port and a threaded portion surrounding the end wall. The fitting comprises a ferrule of resilient deformable material having a forward portion with a wide flat sealing surface which is adapted to mate with and sealingly engage the end wall surrounding the port. The ferrule has a throughbore with a diameter through its rearward portion being sufficient to receive the tubing end and the diameter through the forward portion being smaller than the tubing exterior thereby forming a tubing abutting shoulder within the ferrule. The ferrule is forced into sealing abutment with the end wall of the fluid conducting member and into sealing engagement around the tubing by means of a fastener having a throughbore for receiving the tubing which is flared at its forward end to present conical walls for axially engaging the rearward end of the ferrule. The fastener has a threaded portion for threadedly engaging the threaded portion of the fluid conducting member, thus when the fastener is tightened on the threaded portion of the fluid conducting members, the conical walls of the forward end of the fastener will engage and force the rearward portion of the ferrule inwardly into sealing engagement around the tubing within the ferrule.

6 Claims, 5 Drawing Figures

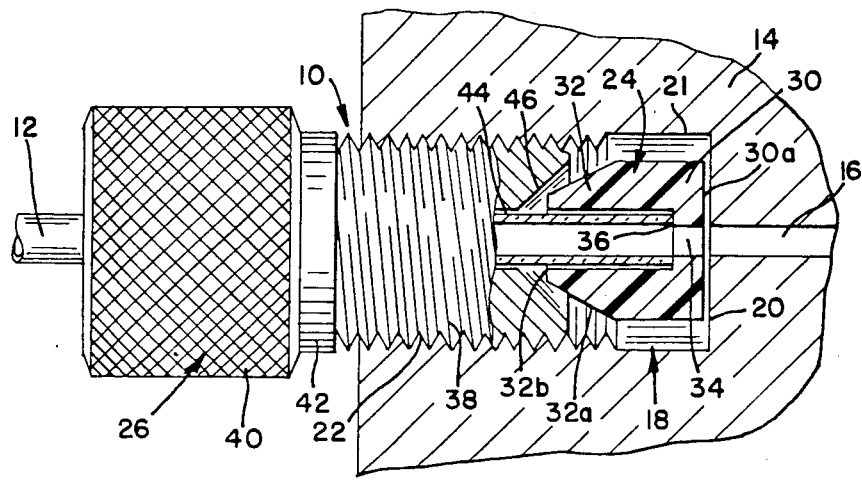
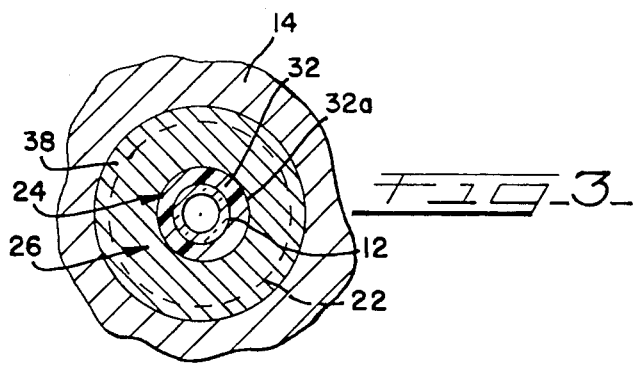
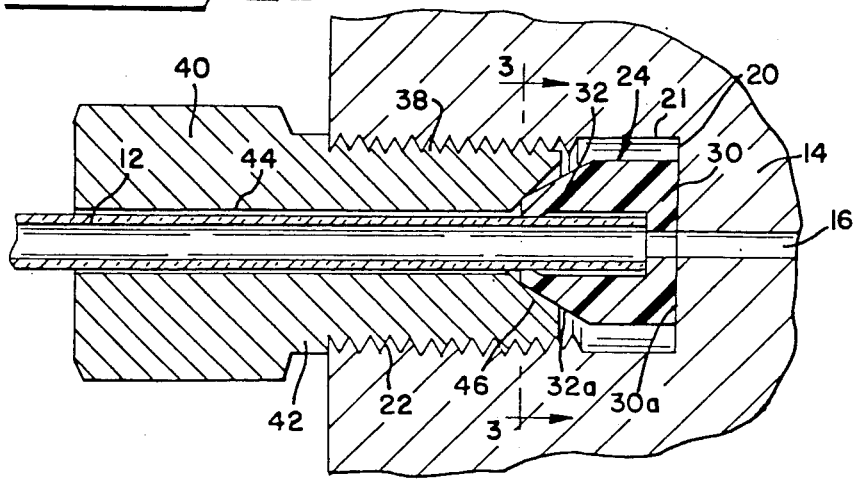

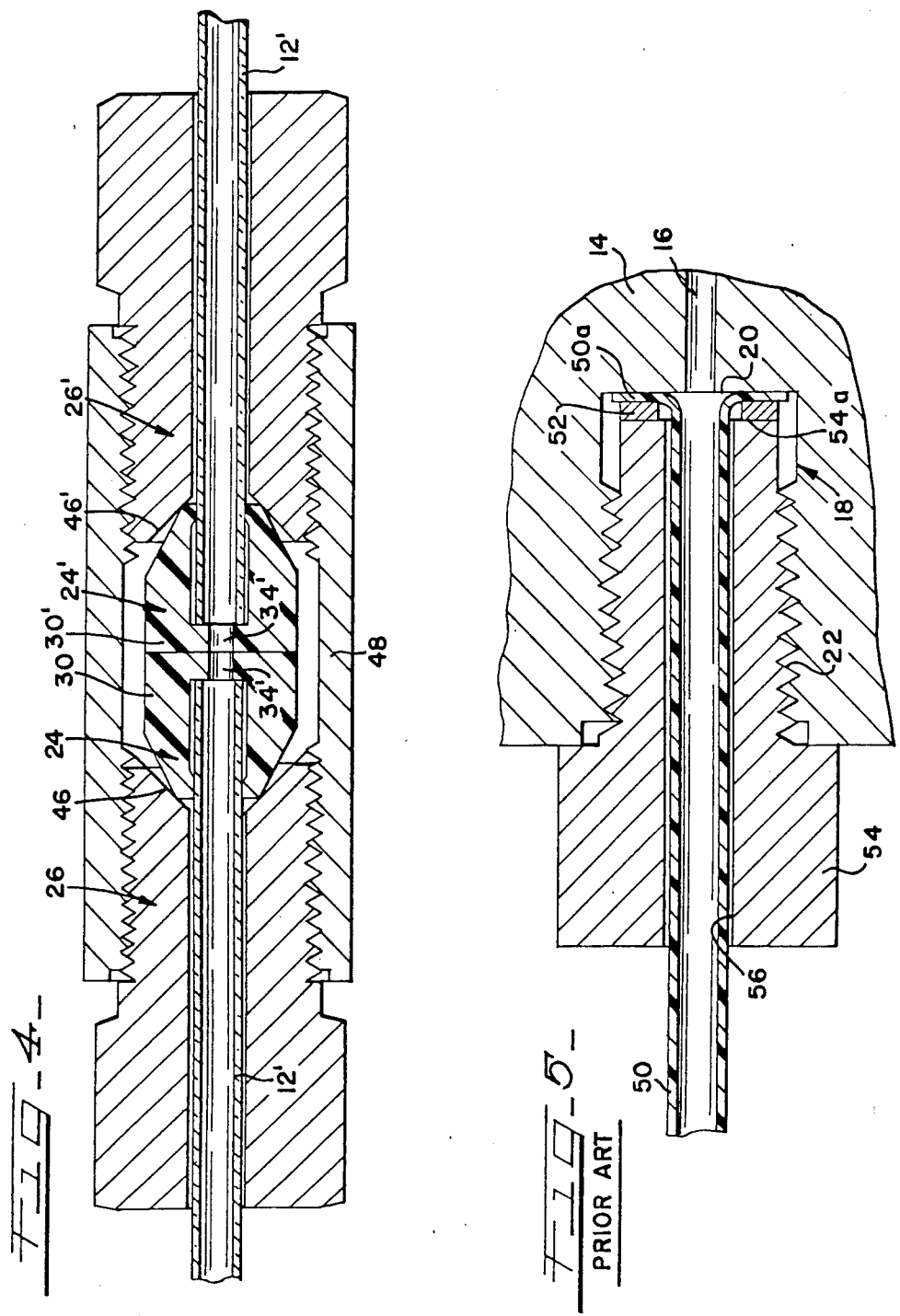

LOW PRESSURE FITTING

BACKGROUND AND SUMMARY OF THE INVENTION

This invention relates to a non-flared fitting for connecting, in fluid sealing relationship, a tubing end to another fluid conducting member, such as a piece of laboratory equipment or another tubing end.

The invention has particular adapation for use in liquid chromatography, providing a low to medium pressure connection, i.e. below about 1,000 p.s.i., between various types of tubing and such laboratory equipment such as chromatography equipment chemical metering devices, amino acid sequencers, or DNA sequencers.

Prior to applicant's invention, most low to medium pressure liquid chromatography and chemical metering systems utilized a fitting in which plastic tubing was flared to form a leak-free seal. To form the connection, the tubing had to be heated and formed using a special flaring tool. Such a procedure was not only bothersome and time consuming, but connections were only possible with tubing made of a thermoplastic material such as Teflon (tetrafluoroethylene) or other heat deformable material. Connections to rigid materials such as glass or metal, or other non-heat deformable plastics required special adapters.

Such connections were not conducive to quick changes and repairs in the laboratory.

The present invention totally eliminates flaring of the tubing as a basis for a seal between the tubing and the fluid conducting member. Thus the problem of connection to rigid tubing is eliminated and the need for flaring procedures and tools or adapters is unnecessary. No modification to the tubing is required. The connection is made by simply sliding a nut and ferrule onto the tubing and tightening into place. The connection thus can be made quickly and easily regardless of the type of tubing being connected.

In accordance with this invention, a fitting is provided for connecting in fluid sealing relationship a tubing end to a fluid conducting member having a fluid port, an end wall surrounding the port and a threaded portion extending from adjacent the end wall. The fitting comprises a ferrule of resiliant deformable material having a forward portion which is substantially wider than the tubing diameter and the end surface of which is configured to mate with and sealingly engage the end walls surrounding the port. The ferrule also has a rearward portion adapted to surround the tubing end. An axial throughbore extends through the ferrule with its diameter through the rearward portion being sufficient to receive the tubing end and its diameter through the forward portion being smaller than the tubing exterior, thereby forming a tube-abutting shoulder at the juncture of the forward and rearward ferrule portions. This is an important aspect of the invention and results in the tubing end being totally contained within the ferrule and being prevented from contact with the fluid conducting member. The second portion of the fitting comprises a fastener which has an axial throughbore for receiving the tubing. The fastener throughbore is flared at the forward end to present a conical fastener wall for axially engaging the rearward end of the ferrule. The fastener has a threaded portion for threadedly engaging the threaded portion of the fluid conducting member so that when the threaded portion is tightened on the threaded portion of the fluid conducting member, the conical forward wall of the fastener will engage and force the rearward end portion of the ferrule inwardly into sealing engagement with the surrounded tubing end and it will also force the forward end portion of the ferrule axially forwardly into flat sealing engagement with the end wall surrounding the port of the fluid conducting member.

Thus, with the present invention, there are two seals provided. The first of these seals is between the ferrule and the tubing at approximately the entry point of the tubing into the ferrule, i.e. at the rearward end of the ferrule. The second seal is between the preferably enlarged flat forward surface of the ferrule with the end walls surrounding the port of the fluid conducting member.

It is preferred that the ferrule have an inwardly tapered rearward end portion for engagement with the outwardly tapered conical throughbore walls of the fasteneing member. It is also preferred that the conical wall taper angle, as measured from the longitudinal axis of the fastener be be substantially greater than the taper angle of the rearward portion of the ferrule. This will cause the inward sealing force exerted by the conical walls at the forward end of the fastener to be concentrated at the extreme rearward end of the ferrule so that the fluid tight seal between the ferrule and the tubing will be at approximately the point the tubing enters the ferrule rearward portion.

BRIEF DESCRIPTION OF THE DRAWINGS

In the drawings:

FIG. 1 is an enlarged side elevational view, partially in cross section, showing a fitting constructed in accordance with this invention, with the tubing, the ferrule and the threaded fastener loosely assembled and inserted into the internally threaded counterbore surrounding the port of a fluid conducting member such as a DNA synthesizer;

FIG. 2 is an enlarged cross sectional view of the fitting of FIG. 1 showing the parts of the fitting and the fluid conducting member after tightening to effect a fluid tight seal;

FIG. 3 is a cross sectional view of the parts taken substantially along line 3—3 of FIG. 2;

FIG. 4 is an enlarged cross sectional view in which two fittings are used in a union connection to connect two tubings together; and FIG. 5 is a side cross sectional elevational view of a flanged fitting system of the prior art.

DETAILED DESCRIPTION OF THE PREFERRED EMBODIMENTS

In FIG. 1 there is shown a fitting 10 for connecting a tubing 12 to a fluid conducting member 14. The fluid conducting member 14 may be a chemical metering system or a piece of equipment employed in liquid chromatography or an amino acid or DNA sequencer, or synthesizer. This piece of equipment has a fluid port 16 the outer end of which terminates in a counterbore 18 having a flat end wall 20 surrounding the port, a cylindrical side wall 21, and internally threaded portions 22 extending outwardly from the side wall 21.

The particular type of connection to this fluid conducting member, which is a piece of laboratory equipment, requires that the connection be able to withstand pressures of on the order of up to 1,000 p.s.i. with the working pressures generally being in the range of between about 400 to 800 p.s.i. In order to accomplish this connection, the fitting 10 comprises a specially designed ferrule 24 and a fastener or nut member 26.

The ferrule 24 is constructed of a resilient, deformable plastic material which has good chemical resistance and tensile strength as well as good mechanical integrity, allowing it to stand up to fluid pressures. The preferred material is chlorotetrafluoreothylene or Kel-F. The ferrule 24 has a cylindrical forward portion 30 which is substantially wider than the diameter of the tubing 12 and the end surface 30a of this forward portion is configured to mate with and sealingly engage the end wall 20 surrounding the port 16 of the fluid conducting member 14. Since in most instances the end wall 20 is a flat planar surface, the end surface 30a of the ferrule forward portion is also a flat planar surface. The ferrule has a rearward portion 32 which is adapted to surround the end of the tubing 12. The ferrule has an axially extending throughbore 34 the diameter of which through the rearward portion 32 of the ferrule is of a diameter sufficient to receive the end of the tubing 12. It is preferred that the fit be a relatively close fit, something of the order between 0.001 and 0.003 inches larger than the diameter of the tubing 12. The throughbore 34 through the forward portion 30 of the ferrule, however, is substantially smaller than the exterior diameter of the tubing 12 and may be as small as, though preferrably no smaller than, the inside diameter of the tubing. This reduction in the diameter of the throughbore 34 from the rearward portion to the forward portion of the ferrule is preferably abrupt and results in the formation of a throughbore shoulder 36 at the juncture of the forward and rearward ferrule portions. As shown in the figures, the end of the tubing 12 will abutt this shoulder 36, thus the tubing end never enters the forward portion 30 of the ferrule and is totally contained within the throughbore of the rearward portion 30 of the ferrule.

The flat planar end surface 30a of the ferrule forward portion surrounding the end of the throughbore 34 is thus an annulus having a sufficient area to effect a fluid tight seal with the end wall 20 surrounding the port 16 of the fluid conducting member 14. The area of this annular surface is preferably between 5 to 8 times the area of the throughbore 34 at its intersection with this surface, providing a large sealing area at the front face of the ferrule.

The rearward ferrule portion 32 is rearwardly and inwardly tapered to form a frustroconical surface 32a at the rearward end of the ferrule terminating at the blunt transverse end surface 32b at the very end of the ferrule. The angle of taper of the frustroconical surface 32a with respect to the horizontal axis of the ferrule 24 is approximately 20°. The rearward tapering of the rearward ferrule portion 32 causes the thinest wall of the ferrule, i.e. between the exterior of the ferrule and the throughbore 34, to be at the very end of the ferrule at the juncture between the conical surface 32a and the blunt end surface 32b.

The fastener 26 is formed of a material such as aluminum or stainless steel which is harder and stronger than the material from which the ferrule 24 is made. The fastener 26 has a forward externally threaded portion 38, a knurled head portion 40 and an intermediate shank portion 42. Extending axially through the fastener 26 is a central throughbore 44. This throughbore is of a diameter sufficient to receive the tubing 12 and is preferably on the order of about 0.003 to 0.005 of an inch larger than the tubing diameter so that the tubing may be easily threaded through the throughbore 44 of the fastener. At the forward end of the fastener, the throughbore 44 is flared outwardly to present a conical wall 46 for axially engaging the rearward end of the ferrule 24 as will be more fully described. It is preferred that the conical wall 46 form approximately a 45° angle with the longitudinal axis of the fastener 26 and the throughbore 44.

In FIG. 1 the parts of the fitting are shown prior to tightening. The ferrule 24 has been inserted onto the end of the tubing 12 and the externally threaded forward end 38 of the fastener 26 has been loosely threaded into and tightened with respect to the internally threaded portion 22 of the counterbore 18 of the fluid conducting member. FIG. 2 shows the parts after the fastener has been fully threaded into the threaded portion 22 of the counterbore 18. As the fastener is tightened down the conical forward wall 46 of the fastener 26 will engage the ferrule rearward portion 32 at approximately the juncture of the frustroconical surface 32a with the blunt transverse end surface 32b. This has two results. First the ferrule will be driven axially forward so that the flat forward face 30a of the forward portion of the ferrule engages the flat end wall 20 surrounding the port 16 of the fluid conducting member 14 forming a fluid tight seal at the interface between the surfaces 30a and 20. As a second result of the engagement of the conical wall 46 of the fastener with the ferrule 24 at the juncture of the frustroconical surface 32a and the blunt end surface 32b, the relatively thin wall of the very end of the rearward portion 32 of the ferrule will be forced radially inwardly into fluid sealing relationship around the end of the tubing 12 within the throughbore 34 at approximately the point the tubing enters the rearward portion of the ferrule. Since the angle of the taper of the conical wall 46 of the fastener is substantially greater than the angle of the taper of the frustroconical surface 32a at the end of the ferrule, the force of the fastener walls against the ferrule will be both radially inwardly at the ferrule end and forwardly to cause the aforemention double seal effect.

This seal between the extreme rearward end of the ferrule 24 and the tubing 12, together with the large annular seal between the surfaces 20 and 30a causes a very tight connection to be made between the tubing 12 and the fluid conducting member 14.

The fitting consisting of the fastener 26 and the ferrule 24 can also be used to connect two tubing sections together as shown in FIG. 4. In that arrangement a ferrule 24 and a fastener 26 on the left-hand side are connected to an similarly constructed ferrule 24' and a fastener 26' in order to achieve a fluid tight connection between the tubing section 12 on the left-hand side and the tubing section 12' on the right-hand side. The two fasteners 26 and 26' are connected together by an internally threaded cylindrical member 48. In such an arrangement, the fluid conducting member may be considered to be the second tubing section 12' having the second ferrule 24' on its end. The second ferrule 24' having a throughbore 34' corresponds to the port 16 of the fluid conducting member 14 illustrated in FIG. 1. The ferrule 24' has a forward portion 30' the end surface of which corresponds to the end wall 20 of the fluid conducting member described and illustrated in the previous embodiment. The two flat forward surfaces of the ferrules 24 and 24' thus abut one another and are forced into tight sealing relationship with one another by the tightening fasteners 26 and 26', respectively. This tightening also causes the rearward end of the ferrule 24 to be formed radially inwardly to sealingly engage around the tubing 12 and the rearward end of the ferrule 24' to be formed inwardly into sealing engagement with the tube 12' by the action of the conical wall surfaces 46 and 46' on the forward ends of the fasteners 26 and 26', respectively, all as described in connection with the previous embodiment.

It may be seen that a very tight connection is achieved by the "two seal" arrangement and this is a very significant advance over the prior art which prior to applicant's invention was being used by the industry. This prior art structure is shown in FIG. 5. In that structure, the tubing 50 which must be constructed of a heat deformable material such as Teflon (polytetrafluoroethylene) is flared at its end 50a by a heated flaring tool (not shown) after a metal ring washer 52 has been inserted on the tubing. This connection employs a fastener 54 having a flat forward end surface 54a and throughbore 56. The fluid conducting member 14 is, of course, the same as previously described with a port 16, a counterbore 18 having an internally threaded portion 22 and a flat forward face 20. The seal of the tubing 50 to the fluid conducting member is a single seal and is accomplished by tightening the fastener 54 until its forward face 54a forces the ring washer 52 downwardly (inwardly) onto the top of the flared end 50a forcing the flared end 50a into tight sealing engagement with the flat surface 20 around the port 16 at the bottom of the counterbore 18.

This type of prior art seal accomplishes a fluid tight connection between the tubing 50 and the port 16, but it requires a special tube flaring tool, an accurate tube flaring operation and utilization of a deformable tubing material. In the absence of a deformable tubing, additional adapters have to be employed in order to achieve the proper connection.

By contrast, the fitting of the present invention does not require any special tubing material, any tube flaring operation, any flaring tools, any modification to the tubing, or any adapters. All that is required is that the ferrule 24 and fastener 26 be slid onto the end of the tubing and tightened into place. Usually the tightening can be done by a simply finger tightening operation. Thus, in the illustrated embodiments, a knurled head 40 is illustrated. If desired, however, a hex head may be employed and this may be desirable in connection with harder tubing such as metal or glass.

The foregoing description of the preferred embodiments has been given by way of example and it will be appreciated by those skilled in the art that various modifications may be made in the structures illustrated and described without departing from the spirit and scope of the invention as hereinafter claimed.

What is claimed is:

1. A fitting for connecting in pressure-tight fluid sealing relationship a tubing end to a fluid conducting member having a pressurizable fluid port terminating in a counterbore having an end wall surrounding said port, a cylindrical side wall and a threaded portion extending outwardly from said side wall; said fitting comprising a ferrule of resisilent deformable material having a forward portion, the outer diameter of which is substantially greater than the outer diameter of the tubing and substantially less than the diameter of the fluid conducting member counterbore and which has an end surface on said forward portion configured to mate with and sealingly engage the end wall surrounding the port, and a rearward portion which is rearwardly tapered, said ferrule having a throughbore with its diameter at least through said rearward portion being sufficient to receive and surround the tubing end; a fastener having a threaded portion for threadedly engaging the threaded portion of said fluid conducting member counterbore and having a throughbore for receiving the tubing, the throughbore being outwardly tapered at the forward end of said fastener to present conical walls for axially engaging said ferrule rearward portion, the taper angle of the conical throughbore walls at the forward end of said fastener being substantially greater than the taper angle of the rearward portion of said ferrule; whereby when the threaded portion of said fastener is tightened on the threaded portion of the fluid conducting member, the conical forward walls of said fastener will engage and force the tapered rearward portion of the ferrule laterally inwardly into sealing engagement around the surrounded tubing end only at approximately the point the tubing enters the ferrule rearward portion and the forward portion of the ferrule will be forced axially forwardly into sealing engagement with the counterbore end wall surrounding the port of said fluid conducting member and in such a sealing engagement said ferrule will be out of contact with the side wall of the counterbore.

2. The structure of claim 1 wherein said ferrule throughbore in said forward portion is smaller than the tubing exterior, thereby preventing said tubing from passing through said throughbore in the forward portion of said ferrule.

3. The structure of claim 2 wherein the taper angle of the conical throughbore walls at the forward end of the fastener is at least approximately double the taper angle of the rearward portion of the ferrule.

4. The structure of claim 2 wherein the change of diameter of said ferrule throughbore is abrupt forming a tube-abutting shoulder at the juncture of said forward and rearward ferrule portions.

5. The structure of claim 1 wherein the end surface of said ferrule forward portion is annular and disposed in a plane substantially perpendicular to the axis of said ferrule throughbore.

6. The structure of claim 5 wherein said ferrule forward portion annular end surface has a sealing area surrounding said throughbore of at least five times the cross sectional area of the largest portion of the throughbore.

* * * * *